United States Patent [19]
Mukaiyama et al.

[11] 3,937,718
[45] Feb. 10, 1976

[54] PROCESS FOR THE PREPARATION OF A CARBOXYLIC ACID ESTER

[75] Inventors: Teruaki Mukaiyama; Masaaki Ueki; Rei Matsueda; Hiroshi Maruyama, all of Tokyo, Japan

[73] Assignee: Sankyo Company Limited, Tokyo, Japan

[22] Filed: Nov. 17, 1970

[21] Appl. No.: 90,420

[30] Foreign Application Priority Data
Nov. 19, 1969 Japan.............................. 44-92684

[52] U.S. Cl....... 260/326.4; 260/471 C; 260/476 R; 260/482 C; 260/488 CD
[51] Int. Cl.².................................. C07D 207/46
[58] Field of Search....... 260/326.3, 488 CD, 476 R, 260/471 C, 482 C

[56] References Cited
OTHER PUBLICATIONS
Mukaiyama et al., J. Am. Chem. Soc. 90:4490–4491 (1968).

*Primary Examiner*—Joseph A. Narcavage
*Attorney, Agent, or Firm*—Flynn & Frishauf

[57] ABSTRACT

An improved and novel process for the preparation of a carboxylic acid ester which comprises reacting a carboxylic acid with an alcohol or a sulfenic acid ester thereof in the presence of a tertiary phosphine and a disulfide of a mercaptoheterocyclic compound containing a nitrogen-carbon double bond with which the disulfide linkage is conjugated.

5 Claims, No Drawings

PROCESS FOR THE PREPARATION OF A CARBOXYLIC ACID ESTER

This invention relates to an improved and novel process for the preparation of a carboxylic acid ester.

Various studies have been made heretofore for the preparation of carboxylic acid esters. The processes which have been most widely accepted include a process which comprises reacting a reactive derivative of a carboxylic acid e.g., acid halide, acid anhydride, etc. with an alcohol, and a process which comprises condensing a carboxylic acid with an alcohol in the presence of a strong dehydrating agent e.g., carbodiimide, etc. However, these prior art processes suffer from several disadvantages. For instance, where a carboxylic acid having a complicated structure is used as a starting material, the preparation of the reactive derivative of a carboxylic acid is often difficult, and where an optically active compound such as an amino acid or peptide of natural origin is used as a starting material, the resulting product may lose optical activity as the consequence of side reaction.

As a result of various investigations into a process which may be conducted under a mild reaction condition without side reaction and may be widely applied to the preparation of the carboxylic acid ester, we have already developed some processes and succeeded to obtain optically pure desired compounds in excellent yield from an optically active compound. According to the prior processes, the carboxylic acid ester is prepared by reacting a carboxylic acid with an alcohol in the presence of a tertiary phosphine, a metal compound and a disulfide or a sulphenyl halide and a base (Japanese Pat. Application Nos. 19269/68 and 85890/68) or in the presence of a tertiary phosphine, a halogen and a base (74921/68) or reacting a carboxylic acid with a sulphenic acid ester in the presence of a tertiary phosphine and an organic metal compound (85888/68). However, these processes have some disadvantages. For instance, the presence of the metal compound is disadvantageous when the starting material or the desired product tends to form fixed chelate compounds with the metal or when the presence of insolubles obstructs a reaction, for example, in case of the preparation of a depsipeptide by a solid phase method which has been recently developed. And, the presence of the halogen is also disadvantageous when the starting material or the desired product contains a group highly reactive to halogen, such as hydroxyphenyl or indolyl. It is, therefore, an object of this invention to provide a novel and improved process for the preparation of carboxylic acid esters, which may be applied to various esterifications without any obstructions as above.

Another object of this invention is to provide a novel and improved process for the preparation of active esters of amino acids which may be used as intermediates for a synthesis of peptide.

Other objects of this invention will be apparent from the following detailed description.

According to the present invention, carboxylic acid esters can be prepared by reacting a carboxylic acid with an alcohol or a sulfenic acid ester thereof in the presence of a tertiary phosphine and a disulfide of a mercaptoheterocyclic compound containing a nitrogen-carbon double bond with which the disulfide linkage is conjugated.

One of the starting materials used in the process of the present invention is a carboxylic acid which may be aliphatic, aromatic or heterocyclic. The kind and type of aliphatic, aromatic or heterocyclic carboxylic acids are not critical, and one may satisfactorily employ as a starting material any carboxylic acids, for example, saturated or unsaturated, straight or branched or long- or short-chain aliphatic carboxylic acids; aromatic monocyclic or polycyclic carboxylic acids which may carry any substituent in the aromatic ring; heterocyclic carboxylic acid with 5- or 6-membered or condensed heterocyclic ring and the like.

The other starting material is an alcohol or a sulfenic acid ester thereof which may be an aliphatic, aromatic or heterocyclic alcohol or an alkyl- or arylsulfenic acid ester thereof. The arylsulfenic acid esters employed in this invention are those substituted or unsubstituted with a nitro group or a halogen atom in the benzene ring. Especially, a nitro-substituted benzenesulfenic acid derivative is preferable. In the present invention, when an amino acid is used as the carboxylic acid and an alcohol having an acidic hydroxy group such a N-hydroxysuccinimide, pentachlorophenol, p-nitrophenol and hydroxyphthalimide is used as the alcohol, there may be prepared an amino acid active ester which is useful as intermediates for the synthesis of peptides or depsipeptides.

If the starting compound used has a reactive functional group such as —COOH, —NH$_2$, —NH—, —SH or —OH as an optional substituent which will not take part in the reaction, it is desirable to block the said functional group with a protecting group which may be easily removed after the intended reaction. For instance, a carboxyl group can be protected in the form of an ester, e.g., lower alkyl or benzyl ester, an amino group can be protected by an acyl group e.g., formyl, trifluoroacetyl, benzyloxycarbonyl, tert.-butoxycarbonyl, tert.-amyloxycarbonyl, nitrobenzenesulfenyl, etc. or a substituted alkenyl group, e.g., 1-methyl-2-acetylvinyl, 1-carboxymethyl-1-propenyl, etc. Imino, mercapto and hydroxy groups can be protected by a benzyl, benzyloxycarbonyl or tetrahydropyranyl group.

Other protecting groups which are commonly known in the art of peptide chemistry are also usable. If such protecting groups are used, the present invention is applicable to the ester formation reaction in the peptide- or depsipeptide synthesis such as enniatin, destruxin, Etamycin and valinomycin.

In accordance with the process of the present invention, the above-referred starting compounds are contacted with the tertiary phosphine and the disulfide in a suitable solvent. As the tertiary phosphine employed in this invention, there may be used any tertiary phosphine selected from aliphatic and aromatic hydrocarbonyl phosphines without specific restriction. Usually, there may be used an easily available and stable tertiary phosphine substituted with the same kind of hydrocarbon such as tributyl phosphine and triphenyl phosphine.

The disulfide used in the present invention is a disulfide of a mercaptoheterocyclic compound containing a nitrogen-carbon double bond with which the disulfide linkage is conjugated and may be symmetric or asymmetric. Representative examples of the disulfide include a disulfide of a six membered mercaptoheterocyclic compound containing one or more nitrogen atoms as a hetero atom and a condensed ring derivative thereof such as 2,2'-dipyridyl disulfide, 4,4'-dipyridyl disulfide, 2,2'-diquinolyl disulfide, 2,2'-dipyrazinyl disulfide, 2,2'-dipyrimidinyl disulfide, 2,2'-diquinoxalinyl disulfide, 4,4'-diquinazolinyl disulfide and 6,6'-diacridinyl disulfide and a disulfide of a five-membered mercaptoheterocyclic compound containing one or more nitrogen atoms as a hetero atom and a condensed ring derivative thereof such as 2,2'-diimidazolyl disulfide, 2,2'-dibenzimidazolyl disulfide, 2,2'-dibenzothiazolyl disulfide, 2,2'-dipurinyl disulfide and 2,2'-bis(1-azaazulenyl) disulfide.

As the solvent, any solvent which does not participate in the reaction can be used. In general, a halogenated hydrocarbon such as methylene chloride and chloroform, dimethylformamide, acetonitrile, etc. is preferably used.

The process of this invention is generally carried out at room temperature but at a higher or lower temperature the reaction may also take place. The reaction time may vary depending upon the sort of the starting compound and reagent used and a reaction temperature. In general, from about several minutes to about tens of hours are required for completion of the reaction.

In the present invention, the disulfide participates with the reaction with each of the other starting materials and the tertiary phosphine at a molar ratio of 1:1:1 when an alcohol is used as one of the starting materials and at a molar ratio of 0.5:1:1 when a sulfenic acid ester is used. Practically, the reaction can, in most cases, be smoothly completed by employing a theoretical amount of the disulfide. But the reaction may be also conducted in the presence of an excess amount of the disulfide.

After completion of the reaction, the desired product is isolated from the reaction mixture by a conventional means. For instance, when a water-immiscible solvent is employed as the reaction solvent, the reaction mixture is washed with water only or successively with water, aqueous sodium bicarbonate, water, dilute hydrochloric acid and water and then dried. The solvent is distilled off and the residue is dissolved in a suitable solvent. The solution is subjected to chromatography to give the desired product. When a water-miscible solvent is employed as the reaction solvent, the solvent is distilled off from the reaction mixture and the residue is dissolved in a water-immiscible solvent. The solution is treated with the same procedure as above to give the desired product.

In the present process, when the ester, especially a depsipeptide is to be synthesized by a solid phase method, one of the starting materials is bounded with an insoluble polymer such as resin and polysaccharide and thus the whole reaction is naturally conducted in a heterogeneous phase, but the reaction condition is the same as in a homogeneous phase.

The following examples are given for the purpose of the illustration of the present invention but should not be construed as a limitation on the scope thereof.

EXAMPLE 1

N-Benzyloxycarbonylglycine benzyl ester

1. A mixture of 2.09 g. of N-benzyloxycarbonylglycine, 2.62 g. of triphenyl phosphine, 2.61 g. of 2-nitrobenzenesulfenic acid benzyl ester, 2.20 g. of 2,2'-dipyridyl disulfide and 50 ml. of methylene chloride is stirred at room temperature for 3 hours. The reaction mixture is washed successively with water, saturated aqueous sodium bicarbonate, water, 0.1 N hydrochloric acid and water and then dried over anhydrous sodium sulfate. The solvent is distilled off. The residue is dissolved in methylene chloride. The solution is subjected to column chromatography using silica gel and eluted with methylene chloride. Distillation of the solvent from the eluate gives 2.51 g. of the desired product melting at 72°C.

2. To a mixture of 1.05 g. of N-benzyloxycarbonylglycine, 0.54 g. of benzylalcohol and 50 ml. of methylene chloride is added dropwise a solution of 1.31 g. of triphenyl phosphine and 1.10 g. of 2,2'-dipyridyl disulfide in 20 ml. of methylene chloride while stirring at room temperature. After completion of the addition, the mixture is stirred at room temperature for an additional 6 hours. The reaction mixture is treated with the same procedure as described above to give 1.36 g. of the desired product melting at 71° – 72°C.

EXAMPLE 2

N-Benzyloxycarbonyl-L-phenylalanine succinimide ester

1. The procedure of Example 1 (2) is repeated, substituting 1.50 g. of N-benzyloxycarbonyl-L-phenylalanine, 1.01 g. of tri-n-butyl-phosphine and 0.58 g. of N-hydroxysuccinimide for the N-benzyloxycarbonylglycine, the triphenyl phosphine and the benzylalcohol, respectively. After completion of the reaction, the reaction mixture is treated with the same procedure as in Example 1 (2) to give 1.31 g. of the desired product melting at 135° – 137.5°C.

$[\alpha]_D^{24}$ −60.0 (C = 1, dimethylformamide)

2. To a mixture of 1.50 g. of N-benzyloxycarbonyl-L-phenylalanine and 0.58 g. of N-hydroxysuccinimide and 50 ml. of methylene chloride is added dropwise a solution of 1.31 g. of triphenyl phosphine and 1.1 g. of 4,4'-dipyridyl disulfide in 20 ml. of methylene chloride while stirring at room temperature. After completion of the addition, the mixture is stirred at room temperature for an additional 6 hours. The reaction mixture is treated with the same procedure as in Example 1 (1) to give 1.21 g. of the desired product.

3. To a mixture of 1.50 g. of N-benzyloxycarbonyl-L-phenylalanine, 0.58 g. of N-hydroxysuccinimide and 50 ml. of methylene chloride is added dropwise a solution of 1.31 g. of triphenyl phosphine and 1.55 g. of 5,5'-dinitro-2,2'-dipyridyl disulfide in 20 ml. of methylene chloride while stirring at room temperature. After completion of the addition, the mixture is stirred at room temperature for an additional 6 hours. The reaction mixture is treated with the same procedure as in Example 1 (1) to give 1.24 g. of the desired product.

4. To a mixture of 1.50 g. of N-benzyloxycarbonyl-L-phenylalanine, 0.58 g. of N-hydroxysuccinimide and 50 ml. of methylene chloride is added dropwise a solution of 1.31 g. of triphenyl phosphine and 1.49 g. of 2,2'-dibenzimidazolyl disulfide in 20 ml. of methylene chloride while stirring at room temperature. After completion of the addition, the mixture is stirred at room temperature for an additional 6 hours. The reaction mixture is treated with the same procedure as in Example 1 (1) to give 1.08 g. of the desired product.

EXAMPLE 3

N-Benzyloxycarbonyl-L-phenylalanine phenylester

A mixture of 2.99 g. of N-benzyloxycarbonyl-L-phenylalanine, 2.02 g. of tri-n-butyl phosphine, 2.70 g.

of 2,4-dinitrobenzenesulfenic acid phenyl ester, 1.10 g. of 2,2'-dipyridyl disulfide and 70 ml. of methylene chloride is stirred at room temperature for 5 hours. The reaction mixture is treated with the same procedure as in Example 1 (1) to give 3.41 g. of the desired product.

Melting point : 102°C.

$[\alpha]_D^{21}$ −29.4° (C = 1, dimethylformamide)

EXAMPLE 4

N-Benzyloxycarbonyl-L-valine methyl ester

A mixture of 2.51 g. of N-benzyloxycarbonyl-L-valine, 2.62 g. of triphenyl phosphine, 1.40 g. of benzenesulfenic acid methyl ester, 1.10 g. of 2,2'-dipyridyl disulfide and 50 ml. of methylene chloride is stirred at room temperature for 5 hours. The reaction mixture is treated with the same procedure as in Example 1 (1) to give 2.30 g. of the desired product.

Melting point : 56°C.

$[\alpha]_D^{17}$ −15.8° (C = 1, ethanol)

EXAMPLE 5

Caproic acid benzyl ester

To a mixture of 1.08 g. of benzylalcohol, 1.16 g. of caproic acid, 2.20 g. of 2,2'-dipyridyl disulfide and 50 ml. of methylene chloride is added dropwise a solution of 2.62 g. of triphenyl phosphine in 20 ml. of methylene chloride while stirring at room temperature. After completion of the addition, the mixture is stirred at room temperature for an additional 3 hours. The reaction mixture is treated with the same procedure as in Example 1 (1) to give 1.9 g. of the desired product boiling at 75°C/0.2 mmHg.

EXAMPLE 6

Benzoic acid t-butyl ester

To a mixture of 0.74 g. of t-butanol, 1.22 g. of benzoic acid, 3.32 g. of 2,2'-dibenzothiazolyl disulfide and 50 ml. of methylene chloride is added dropwise a solution of 2.62 g. of triphenyl phosphine in 20 ml. of methylene chloride while stirring at room temperature. After completion of the addition, the mixture is stirred at room temperature for an additional 5 hours. The reaction mixture is treated with the same procedure as in Example 1 (1) to give 1.35 g. of the desired product boiling at 75°C/3 mmHg.

EXAMPLE 7

O-Nitrophenylsulphenyl-L-glutamine succinimide ester

To a solution of 0.750 g. of o-nitrophenyl sulphenyl-L-glutamine, 0.288 g. of N-hydroxysuccinimide and 0.550 g. of 2,2'-dipyridyl disulfide in 4 ml. of dimethylformamide is added to 0.655 g. of triphenyl phosphine and the mixture is stirred at room temperature for 4 hours. To the reaction mixture is added 100 ml. of isopropanol at 0°C with stirring. The produced precipitates are washed successively with isopropanol, methylene chloride and ether and then dried to give 0.735 g. of the desired product.

Melting point : 146° − 147°C.

$[\alpha]_D^{23}$ −59.8 (C = 2, dimethylformamide)

Analysis:

Calculated for $C_{15}H_{16}N_4O_7S$ : C, 45.50; H, 4.07; N, 14.14; S, 8.07

Found : C, 45.73; H, 4.35; N, 14.22; S, 8.03

EXAMPLE 8

N-Benzyloxycarbonyl-L-glutamine pentachlorophenyl ester

To a solution of 0.700 g. of N-benzyloxycarbonyl-L-glutamine, 0.665 g. of pentachlorophenol and 0.55 g. of 2,2'-dipyridyl disulfide in 20 ml. of dry acetone is added an acetone solution of 0.655 g. of triphenyl phosphine with stirring at 0°C. The produced precipitates are recovered by filtration and washed successively with a 3 % sodium bicarbonate solution, water and ether and recrystallized from a mixture of dimethylformamide and methanol to give 0.952 g. of the desired product.

Melting point : 182° − 184.5°C.

$[\alpha]_D^{20}$ −17.3 (C = 1, dimethylformamide)

Analysis:

Calculated for $C_{19}H_{15}N_2O_5Cl_5$ : C, 43.17; H, 2.86; N, 5.30; Cl, 33.54.

Found : C, 43.09; H, 2.81; N, 5.32; Cl, 33.81

EXAMPLE 9

N-Benzyloxycarbonyl-L-asparagine pentachlorophenyl ester

The procedure in Example 8 is repeated employing 0.665 g. of N-benzyloxycarbonyl-L-asparagine, 0.665 g. of pentachlorophenol, 0.655 g. of triphenyl phosphine and 0.55 g. of 2,2'-dipyridyl disulfide to give 0.953 g. of the desired product.

Melting point : 167° − 185°C.

$[\alpha]_D^{20}$ −26.7° (C = 1, dimethylformamide)

Analysis:

Calculated for $C_{18}H_{13}N_2O_5Cl_5$ : C, 42.01; H, 2.55; N, 5.44; Cl, 34.45

Found : C, 41.73; H, 2.63 N, 5.36; Cl, 34.17

EXAMPLE 10

N-Benzyloxycarbonyl-L-nitroarginine pentachlorophenyl ester

To a solution of 0.883 g. of N-benzyloxycarbonyl-L-nitroarginine, 0.665 g. of pentachlorophenol and 0.55 g. of 2,2'-dipyridyl disulfide in 30 ml. of tetrahydrofuran is added dropwise a tetrahydrofuran solution of 0.655 g. of triphenyl phosphine while stirring at 0°C. The mixture is stirred at 0°C for further 3 hours. After completion of the reaction, the reaction solvent is distilled off and the residue is dissolved in methylene chloride. The solution is washed with a 5 % sodium bicarbonate solution and water. The solution is dried over anhydrous sodium sulfate and filtered. The filtrate is left to stand overnight at −10°C. The produced precipitates are recrystallized from a mixture of tetrahydrofuran and ether to give 1.07 g. of the desired product.

Melting point : 109° − 111°C.

$[\alpha]_D^{30}$ −14.2° (C = 1.01; dimethylformamide)

Analysis:

Calculated for $C_{20}H_{18}N_5O_6Cl_5$ : C, 39.92; H, 3.02; N, 11.64; Cl, 29.46
Found : C, 40.19; H, 3.03; N, 11.35; Cl, 29.70

EXAMPLE 11

N-Benzyloxycarbonyl-L-phenylalanine 8-hydroxyquinoline ester

To a suspension of 149.5 mg. of N-benzyloxycarbonyl-L-phenylalanine, 72.5 mg. of 8-hydroxyquinoline, 110 mg. of 2,2'-dipyridyl disulfide, 225.5 mg. of mercury diphenylphosphine-p-benzenesulfonate in 20 ml. of dry methylene chloride is added dropwise a solution of 57 mg. of N-ethylpiperidine in 10 ml. of methylene chloride while stirring at room temperature. The mixture is stirred at room temperature for further 5 hours. The reaction mixture is filtered and the filtrate is washed successively with 0.5 N sulfuric acid, water, a 3 % sodium bicarbonate solution and water and dried over anhydrous sodium sulfate. The solution is distilled off and the residue is recrystallized from a mixture of ethyl acetate and petroleum ether to give 149 mg. of the desired product.

Melting point : 138.5° – 139.5°C.
$[\alpha]_D^{25}$ −70.6° (C = 2, dimethylformamide)

What is claimed is:

1. A process for the preparation of a carboxylic acid ester which comprises reacting an aliphatic, aromatic or heterocyclic carboxylic acid with an aliphatic, aromatic or heterocyclic alcohol or an alkyl- or aryl-sulfenic acid ester thereof in the presence of an aliphatic or aromatic hydrocarbonyl tertiary phosphine and a disulfide of a mercaptoheterocyclic compound containing a nitrogen-carbon double bond with which the disulfide linkage is conjugated.

2. A process for the preparation of an amino acid active ester which comprises reacting an aliphatic, aromatic or heterocyclic amino acid with an aliphatic, aromatic or heterocyclic alcohol having an acidic hydroxy group in the presence of an aliphatic or aromatic hydrocarbonyl tertiary phosphine and a disulfide of a mercaptoheterocyclic compound containing a nitrogen-carbon double bond with which the disulfide linkage is conjugated.

3. A process as claimed in claim 2 wherein said alcohol is selected from the group consisting of N-hydroxysuccinimide, pentachlorophenol, p-nitrophenol and hydroxyphthalimide.

4. A process as claimed in claim 1 wherein said disulfide of a mercaptoheterocyclic compound is selected from the group consisting of 2,2'-dipyridyl disulfide, 4,4'-dipyridyl disulfide, 5,5'-dinitro-2,2'-dipyridyl disulfide and 2,2'-dibenzothiazolyl disulfide.

5. A process as claimed in claim 1 wherein said tertiary phosphine is a trialkyl phosphine or triphenyl phosphine.

* * * * *